United States Patent [19]

Li

[11] Patent Number: 4,785,954

[45] Date of Patent: Nov. 22, 1988

[54] WELDING MASKHOLDER

[76] Inventor: Edward K. Li, No. 3, Lane 21, Sec. 2 Jong-Iang Road, Tuu Cherng Hsiang, Taipei Hsien, Taiwan

[21] Appl. No.: 921,614

[22] Filed: Oct. 22, 1986

[51] Int. Cl.$^4$ ............................................... B23K 9/32
[52] U.S. Cl. ........................................... 219/147; 2/8; 219/138
[58] Field of Search .................... 228/57; 2/8; 219/147

[56] References Cited

U.S. PATENT DOCUMENTS 2,105,018  1/1938  Tatter ................................... 219/147

FOREIGN PATENT DOCUMENTS

1080730  4/1960  Fed. Rep. of Germany .
554941  1/1957  Italy .
34364  11/1934  Netherlands .
260738  8/1949  Switzerland .

Primary Examiner—Nicholas P. Godici
Assistant Examiner—Carmine Cuda
Attorney, Agent, or Firm—Asian Pacific International Patents & Trademark Office

[57] ABSTRACT

A special welding apparatus comprises welding pliers and a head shield, which may be attached together by means of an engaging groove, a pressure ball, a fixed ring, a fixed hook and a hook seat, or may be separated from each other. The colored goggle assembly has a sliding mechanism; when a key on the handle of the head shield is pressed down, the colored goggle will slide away from the window, and when the key is released, the colored goggle will be moved back over the window.

3 Claims, 6 Drawing Sheets

WELDING MASKHOLDER

BACKGROUND OF THE INVENTION

This invention relates to a special welding apparatus, particularly a welding shield with a movable goggle. The colored goggle can be moved to cover and uncover the transparent goggle window.

In modern industry, a product should have not only a better quality, but also a lower cost and price. In order to achieve the aforesaid goal, a better apparatus or tool is essential to the modern industry, i.e., a tool should be practical, durable, of precision, and should have more functions so as to lower the cost, to protect the user, and to increase the working efficiency.

A welding process is often required in many aspects in modern industry. The welding quality and efficiency are directly impacting on the manufacturing costs. In electric welding, most is done manually and it is certainly believed that the manual welding operation will continue to be used in the respective industries owing to many reasons, such as some parts having irregular specifications, the factories or working sites having different facilities and scales. In other words, a full automatic welding operation can not be adopted in all factories. Therefore, there exists the need to develop a welder's safety, to lower the cost and to enhance the quality of welded products, and to elevate the welding efficiency.

The existing electric welding head shields may be classified into two kinds: the hand-held type and the headmounted type. The latter type is further classified into three classes: a fixed colored goggle, a movable colored goggle type (i.e., the colored goggle on the window can be covered and uncovered), and a type with helmet. When using the head-mounted type of head shield to fall down from the top portion so as to position the window in front of the eyes for protection purposes. The welder will have a free hand to hold the work piece; therefore, the head-mounted type of shield can, under certain circumstances, increase the working efficiency, and it is used by many factories and welders in the developed countries.

According to the welding experiences, an intense welding arc and a toxic smoke may be simultaneously generated during a welding operation. Most of the conventional head shields are designed with a conic monopod shape, from which the smoke—once it entered—is not easily exhausted. Consequently, at the face of the welder there will accumulate a lot of smoke, which would cause some occupational diseases, such as bronchitis, pink eye, and respiratory ailments. The welder is susceptible to suffer from such diseases when working at a place that has a poor ventilation system. Moreover, if the welder does not wear a normal helmet, the situation may become worse. If the welder is required to wear a helmet during a welding operation, a regular and professional helmet has to be used. A helmet is usually called a melon rind type of helmet by welders; a helmet without visor should not be used because it is unable to protect the welder's ears and nose in case some harmful stuffs strike him on the head.

When using a hand-held type of head shield, the welder would have difficulties in holding the work piece with one hand, while his other hand is used to make spot welding. Usually, the welder closes his eyes to prevent the intense welding arc from radiating into his eyes, but his face gets exposed to the intense welding arc. Experience has proved that the welder after long time exposing to such intense welding arc would suffer from dry skin, swollen skin around the eyes, peeling skin, eye diseases, or skin cancer. One might say that there are still many welders working in the conventional manner without suffering any aforesaid diseases; in fact, they are either not aware of the danger due to lack of knowledge, or having no choice.

The following is a real example for reference. There is a factory located in a certain processing zone in Taichung area, which is specialized in doing mechanical body work for their customers. One day a department of the factory accepted an order to make a lathe scrap tank. The material for the tank was a steel sheet of 1 mm thick. After being measured and cut, the steel sheet was bent into the required form; them, the side board and pipe joints thereof were added. Since it was a small order with irregular specifications and lower processing price, there was no particular working clamps being designed or made; further, the welders of that factory were used to conduct welding with the hand-held type of head shields (in fact, most of the welders in Taiwan use that kind of head shield). To make the scrap tank as mentioned above, the various parts thereof had to be assembled together in position first by means of spot welding; then, a regular leak-proof welding was conducted, followed by finishing and hole-drilling processes. During the spot welding process, one hand of the welder had to hold the welding pliers, whereas the other hand held the work piece; therefore, the experienced welder closed his eyes to do the welding work. As a result of the radiation of the intense welding arc, it was discovered by the inventor that all of the welders from that factory suffered from serious peeling skin; some of them even needed to see a doctor for their swollen eye skin. Some of then might have suffered from skin cancer. Many of the similar aforementioned cases were discovered by the inventor during his working travelling, but it can not be fully described herein because of limited pages.

Nowadays, efficiency is the main issue in our daily lives. Naturally, the welding business is under serious competition; welders seem to have less or no time to pre-fix the work piece before putting on the head shield and starting to weld the work piece. One might ask why welders do not use the head-mounted type of shields to avoid the aforesaid injuries. In real work sites, welders usually do many things one after another, such as handling the materials, welding, moving articles from one place to another, or climbing up and down around a big mechanical structure. In that case, the head shields often slide down to block the vision of wearers. Welder may put on or remove the head shields as the case may be, but they may feel inconvenient to them in terms of work efficiency. In fact, the conventional head-mounted type of head shields is not quite good to use.

Another instance was personally seen by the inventor while he was in San Francisco. The inventor once worked in a shipyard as a welder. According to the regulations of the insurance company, every worker working in a ship must wear a helmet which was a special type of helmet with no visor, and the American welders called it a melon-rind type of helmet. One day, the inventor saw a piece of wood strike a worker on one of his ears, who was seriously injured; that worker was a welder working on a hanging scaffold. The inventor believed that the head shield of that special type of helmet was not a good one. If it is tightly worn on the head, the wearer would have a headache. If it is loosely worn on the head, the window does not usually fall in its correct position after the head shield is pulled down; further, the head shield fallen down often swings laterally. The inventor also inquired the point of views of the American welders on that type of helmet; they all agreed with my opinion. Consequently, the inventor brought a hand-held type of head shield to the work site to use it as a helmet with visor. The inventor had to hold the work piece with one hand and the welding pliers with the other hand. In that case, the inventor had to close his eyes to perform the welding operation. After working for one day, he had a seriously dry feeling on his face, and had seriously swollen skin around his eyes the next morning; then his skin peeled off after several days. The insurance company said no damages could be claimed because the insurant did not follow the regulations to wear a head shield.

Summarizing the aforsaid facts, it is evident that the current two types of head shields all have their own drawbacks. The inventor has over 20 years of welding experiences; during that period, no one has paid attention to these drawbacks. Since the inventor is also a businessman, and has understood that the manufacturing cost and the quality of a product would directly relate to the success of an enterprise. If an enterprise is provided with the best tools, it would be instrumental to its success.

SUMMARY OF THE INVENTION

In view of the aforesaid facts, the inventor has developed an improved welding shield, which has been tested and proved to be practical in welding operation, and is named a "WELDING MASK HOLDER".

In this welding apparatus, the pliers and the head shield can easily be assembled together or disassembled by means of an engaging groove, a pressure ball, a fixed ring, a fixed hook and a hook seat. The colored goggle is furnished with a sliding mechanism. After the key on the handle is pressed, the colored goggle will slide away from the window so as to let the welder see, via the transparent plain glass, the work piece and the position or angle of the welding rod. After the key is released, the colored goggle will slide over the window so as to let the welder conduct spot welding or line welding. As soon as the two work pieces are welded together, the welder will have a free hand to hold the work piece or to act otherwise. Since the present invention can be used as welding pliers, a head shield and a plain optical glass to protect the welder's eyes and face, it will also be able to elevate the work efficiency.

BRIEF DESCRIPTION OF THE DRAWINGS

In view of explaining more clearly the characteristics of the invention, but merely as an example and without the intent of limitation, a preferred form of embodiment will be described hereinafter with reference to the appended drawings in which.

DETAILED DESCRIPTION

As shown in the attached drawings, the welding shield and pliers with a movable goggle 20 according to the present invention comprises a head shield 21 according to the present goggle 22, a lower transparent frame 23, a first, welding plier handle or lever handle 24, a zigzag-rule type of welding pliers 25, springs 26 and 26', a window control key 27, a shield handle 28, a welding plier handle 29, a fixing ring 30, screws 31, an upper transparent frame 32, a pulley 33, a steel cord 34, a fixed ring 35, a goggle sliding rod 36, a bearing 37, a goggle frame 38, a nut 39, a control key sliding rod 40, a sliding rod seat 41, a window 42, a wire hole 43, a fixed hook 44, a hook seat 45, a pressure ball 46, a sliding groove 47, movable balls 48, an engaging groove 49, a conductor 50, a shaft 51 and a protective layer 52.

Figure 1:
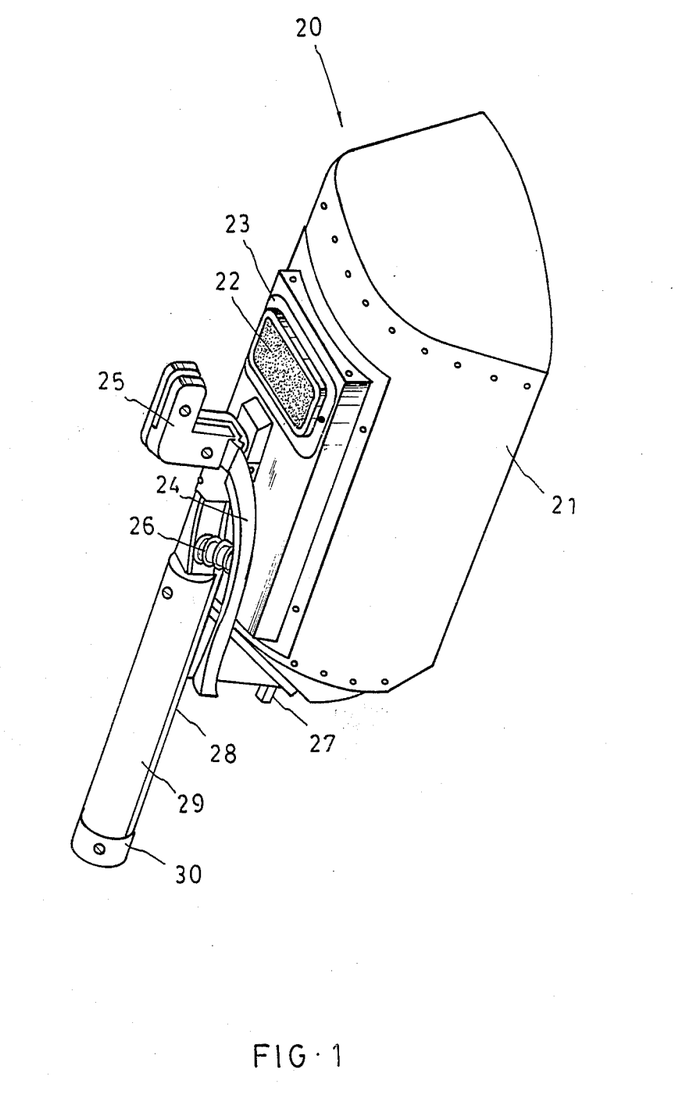
FIG. 1 is a perspective view of the present invention, showing the head shield and the welding pliers being assembled together.
Figure 2:
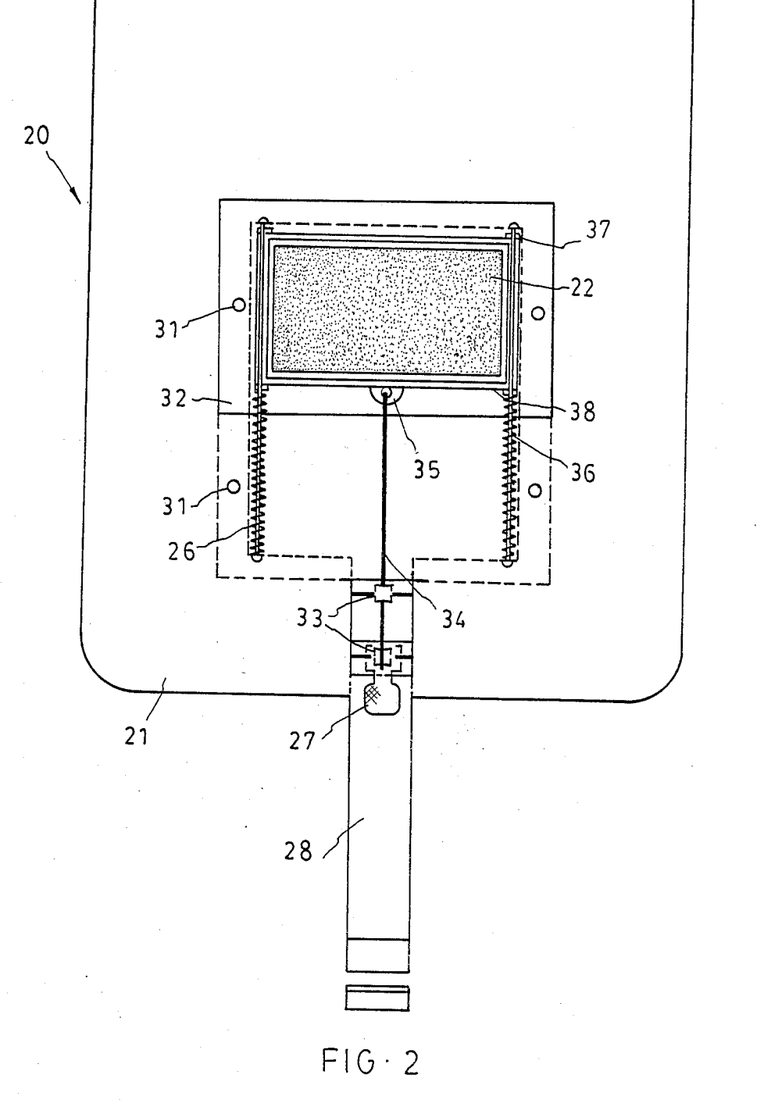
FIG. 2 is a rear view of FIG. 1, showing the control mechanism of the goggle window.
Figure 3:
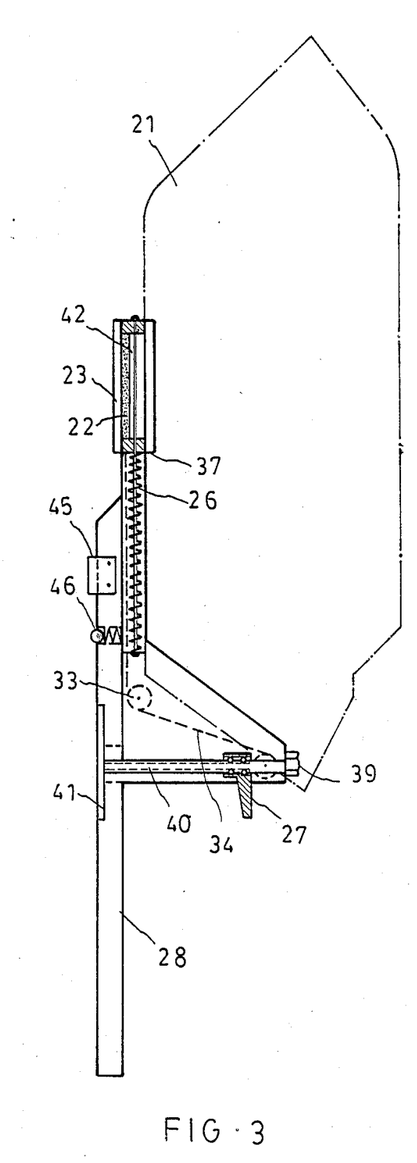
FIG. 3 illustrates an operational view of the control mechanism of the goggle window, particularly showing the goggle being pushed upwards to close the window.
Figure 4:
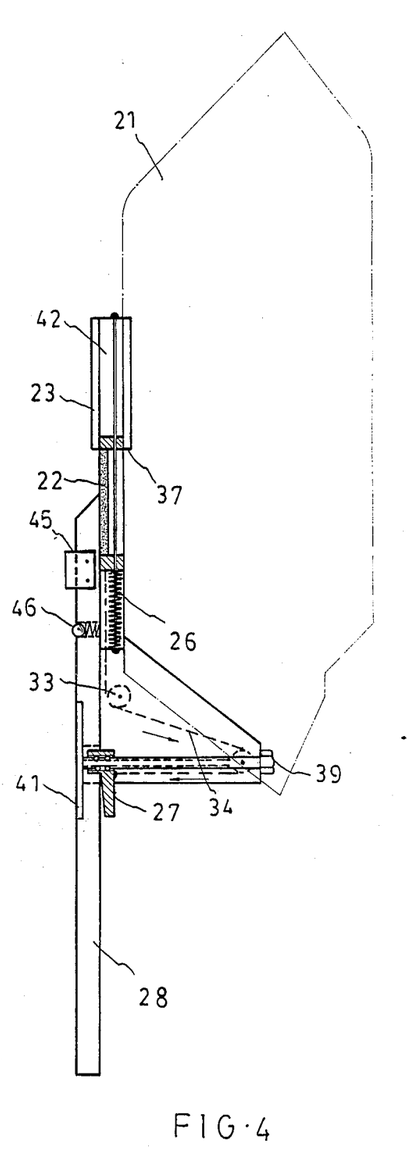
FIG. 4 is a side view of the present invention, showing the goggle being pulled away from the goggle window.
Figure 5:
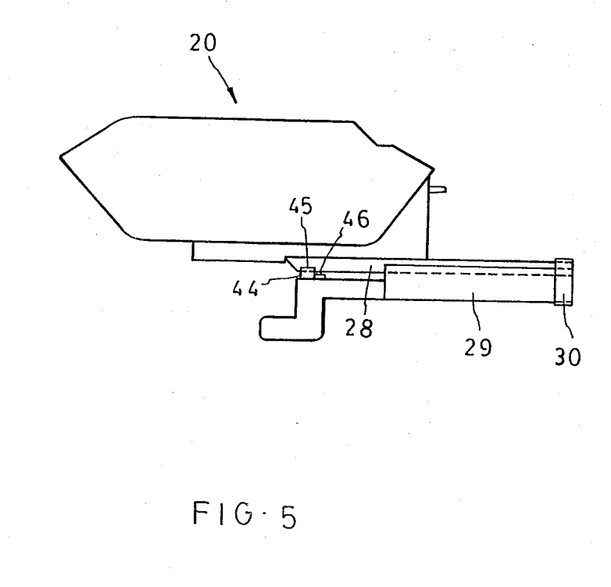
FIG. 5 is a right side view of FIG. 1.
Figure 6:
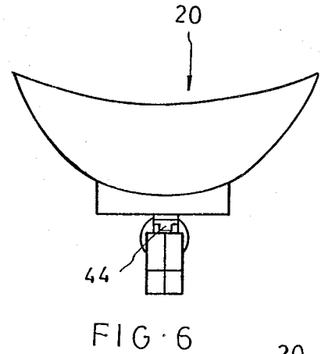
FIG. 6 is a top view of FIG. 1.
Figure 7:
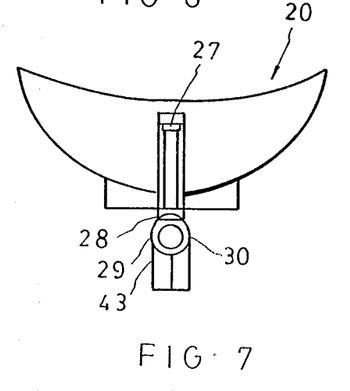
FIG. 7 is a bottom view of FIG. 1.
Figure 8:
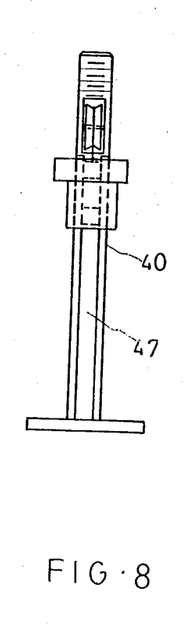
FIG. 8 is a front view of the goggle window control mechanism, showing the goggle window control key being set at the upper dead point.
Figure 9:
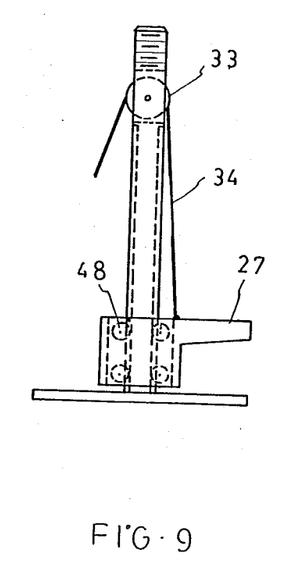
FIG. 9 is a side view of the goggle window control mechanism, showing the goggle window control key being set at the lower dead point.
Figures 10, 11, 12:
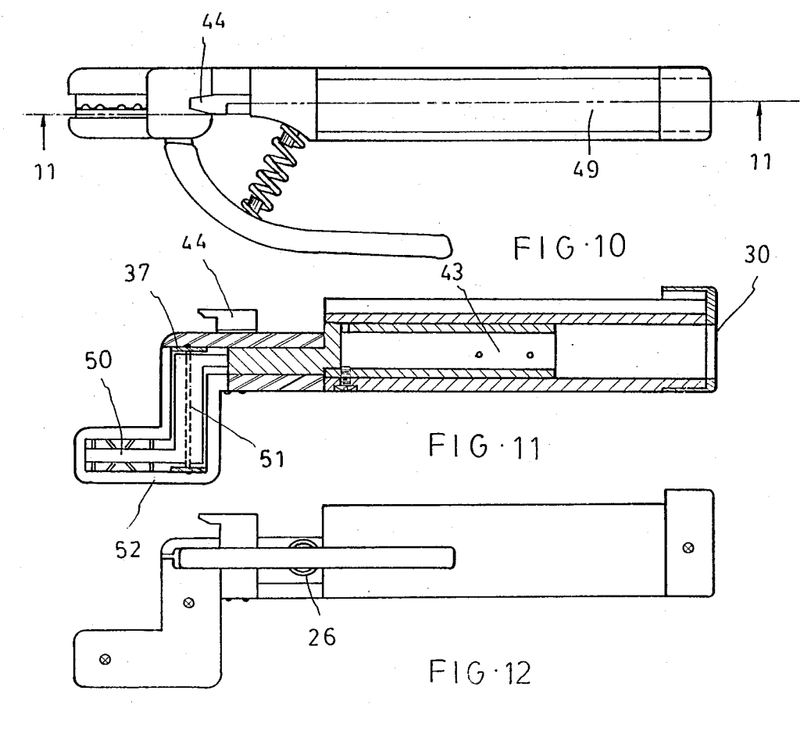
FIG. 10 is a rear view of the welding pliers.
FIG. 11 is a sectional view along line 11—11 in FIG. 10.
FIG. 12 is a side view of the welding pliers.
Figure 13:
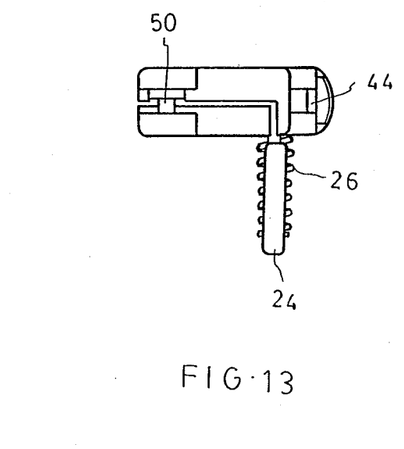
FIG. 13 is a top view of the welding pliers.
Figure 14:
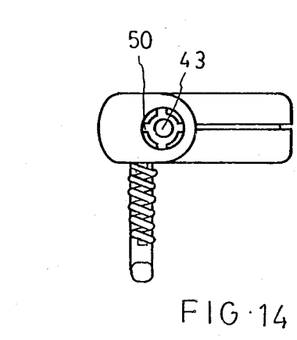
FIG. 14 is a bottom view of the welding pliers.

Upon using the welding shield and pliers with the movable goggle, one of the user's hand is holding the work piece, while his other hand is holding the welding pliers 25 and the head shied 21 assembled together (as shown in FIGS. 5, 6 and 7), and simultaneously presses down the window control key 27 on the shield handle 28 so as to have the goggle 22 slid away from the goggle window 42 as shown in FIG. 4, and to let the user see clearly, via the window 42, the work piece to be pointed at the spot with the welding rod; then, releases the goggle window control key 27. After letting the welding rod touch the work piece, he is ready for either spot welding or line welding.

Since one of the user's hands holds the welding pliers 25 and the head shield 21 which are attached to each other, his other hand can hold the work piece or do other work. Since the user's face is protected with the head shield 21, the welding arc would not injure his face; he can also watch the welding condition of the work piece via the colored goggle 22 so as to maintain a better welding quality. In the past, a welder had to close his eyes while making a spot welding to test a stainless steel work piece; in that case, the work piece is susceptible to be burnt through or not welded firmly; occasionally, the welding arc might be discontinued or the welding rod might be stuck on the work piece. As a result of the stainless steel, the cooled welding scales might fly randomly out of the work piece to hit the eyes of the welder. After one welding rod has been used up, the welding scales of the last welded part on the work piece have to be removed with a tool so as to maintain a better welding quality. In fact, few welders wear the head shield for doing these removals; some of them might wear a pair of eye glasses, but the high temperature welding scales might fly out to hit the face and cause an injury. Therefore, many welders are afraid to weld the stainless work piece. The aforesaid case can be removed by using a feature of the present invention, a welding shield and pliers with the movable goggle 20.

The welding shield and pliers with the movable goggle 20 comprises the engaging groove 49, fixing ring 30, fixed hook 44, hook seat 45, and pressure ball 46. Referring to FIGS. 3-7 and 10-14, it is shown that the two parts after being engaged together would not be separated automatically under normal condition because of the action of the pressure ball 46. A sample of the present invention made by the inventor was tested for about 500 times of engaging and disengaging, and was also tested by hitting the welding shield with force until the pressure ball 46 scratching a vivid scratch on the fixed hook 44; the whole welding shield never showed any deformation or other abnormal state. It is evident that a tool like the present invention can withstand the rough use of a rough welder; in other words, the welding shield according to the present invention can, under normal condition, be used for a considerable long time.

The goggle window control mechanism of the welding shield and pliers with the movable goggle 20 is operated by means of a number of parts which include control key 27, movable balls 48, sliding groove 47, sliding rod 40, goggle sliding rod 36, steel cord 34, and pulley 33, all of which are driven by spring 26 as shown in FIGS. 2, 3, 4, 8 and 9. During the aforesaid 500 tests, it has been proved that the whole sliding system can withstand the tests.

The user of the welding shield and pliers with a movable goggle according to the present invention needs only a little training, and everybody can use it after a very short time of practice. It is strong and durable for long time use. Upon the colored goggle being moved away from the window, the shield is just like a general shield with welding pliers; upon the colored goggle being mounted over the window, the two parts are attached together; in other words, the present invention can be used as either a colored goggle or a plain optical glass. When using the shield according to the present invention, the user will have a free hand to hold the work piece or to do other motion. Upon pressing down the control key, the colored goggle will be moved away from the window so as to let the user see the work piece and the position of the welding rod through the window; upon the control key being released, the colored goggle will slide over the window to let the user watch the welding state without injuring his eyes and face. The inventor deems that the present invention is a valuable tool to the industry.

The aforesaid embodiment is used for describing the objects, the features and functions of the present invention. Any person skilled in the art may make a change or modification to the aforesaid embodiment in accordance with the aforesaid description without being deemed to deviate from the spirit and scope of the present invention; therefore, the scope of the present invention may only be limited by the claims attached.

I claim:

1. A welding head shield and welding rod pliers characterized in that said shield and said pliers can be combined into one unit, and said pliers and said shield can also be separated from each other as discrete units;

said head shield comprising
    a shield body with a window opening formation;
    a transparent window pane in said window opening formation;
    a shield handle operatively connected at said shield body;
    a hook seat secured at said shield handle;
    a pressure ball seated at said shield handle;
    a spring located at said shield handle to bias said pressure ball into a lock position, and said spring being adapted to be compressed to allow release of said pressure ball from the lock position into a neutral position;
    a welding rod pliers with a pair of plier jaws for operatively securing a welding rod therebetween, said pliers also including a pliers handle with an engaging groove formation, said pliers also including a lever handle connected at least at one pliers jaw for actuation of said pliers, and said pliers jaws each having a zigzag profile surface;
    a fixed hook at said pliers adapted to be connected at said hook seat for securing said pliers at said head shield;
    a fixed ring for securing said shield handle and said plier handle at conterminous ends thereof;
    a protective layer on said pliers jaws;
    a conductor connected to said jaws;
    at least one pivot shaft for said jaws; and
    a control mechanism for selectively covering and uncovering said transparent window pane, said control mechanism including
    a rod seat secured at said shield handle;
    a rod, said rod having a first end and a second end, with said first end being connected at said rod seat;
    p1 a window control key reciprocatingly movable arranged on said rod and adapted to be moved between a first position in which said window pane is covered and a second position in which said window pane in uncovered;
    a plurality of movable balls for guiding said window control key during its movement on said rod;
    a pulley connected at the second end of said rod;
    at least one colored goggle pane slidingly arranged at said head shield body for covering and uncovering said window pane in said shield body;
    a frame connected at said goggle pane, said frame having guide formations for respective slide rods;
    a pair of goggle slide rods for guiding said goggle frame when moving said colored pane for covering and uncovering said transparent window pane;
    for each slide rod, a spring adapted to bias said goggle frame;
    a steel cord connected with one end to said goggle frame and connected with its other end to said control key;
    wherein upon said control key being moved along said rod, said steel cord pulling said frame and said colored goggle into the uncovering position along said goggle slide rods against the tension of respective spring at a respective slide rod, said transparent window pane is uncovered and a welder can see the work piece through said transparent window pane under full protection of his eyes and face; and
    wherein upon said control key being released, said colored goggle is moved to cover said transparent window pane in response to the action of a respective spring at a respective slide rod, and the welder can see the welding portion and the welding rod flame without being injured by the welding flame.

2. The rod of claim 1 which includes at least one sliding groove formation in said rod for guiding said moveable balls in the manner of an axial ball-bearing guide.

3. The welding shield according to claim 1, wherein the portion of said head shield above said welding pliers is rearwardly inclined with respect to the front face of said shield.

* * * * *